(12) United States Patent
Roulier et al.

(10) Patent No.: US 6,416,751 B1
(45) Date of Patent: Jul. 9, 2002

(54) COSMETIC AND/OR DERMATOLOGICAL POWDER, PROCESS FOR ITS PREPARATION AND ITS USES

(75) Inventors: Véronique Roulier, Paris; Dominique Bordeaux, Longpont sur Orge, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/243,495

(22) Filed: Feb. 3, 1999

(30) Foreign Application Priority Data

Feb. 3, 1998 (FR) .............................. 98 01219

(51) Int. Cl.$^7$ .......................... A61K 6/00; A61K 7/00; A61K 7/035
(52) U.S. Cl. ........................................ 424/69; 424/401
(58) Field of Search .................. 424/69, 401; 514/937, 514/938

(56) References Cited

U.S. PATENT DOCUMENTS 5,223,559 A * 6/1993 Arraudeau et al. ........... 524/47
5,871,756 A * 2/1999 Jeffcoat et al. .............. 424/401
5,961,990 A * 10/1999 Delrieu et al. ............... 424/401

OTHER PUBLICATIONS

Derwent–Acc–No: 1999–471260.*

* cited by examiner

Primary Examiner—Thurman K. Page
Assistant Examiner—S. Howard
(74) Attorney, Agent, or Firm—Oblon, Spivak, McClelland, Maier & Neustadt, P.C.

(57) ABSTRACT

A cosmetic and/or dermatological powder comprising from 5 to 70% of modified starch and from 30 to 95% of oily phase comprising at least one oil. The present invention also relates to a process for manufacturing a cosmetic and/or dermatological powder comprising at least one modified starch and an oily phase, by (1) preparing an oil-in-water dispersion by mixing an oily phase comprising at least one oil in an aqueous phase comprising at least one modified starch, the oily phase/starch weight ratio ranging from 3:7 to 19:1, and (2) dehydrating the dispersion in order to obtain the powder. The powder may be used just as it is and is useful in particular to care for, cleanse, remove make-up from, make up and/or treat the skin, mucous membranes and/or the scalp.

25 Claims, No Drawings

COSMETIC AND/OR DERMATOLOGICAL POWDER, PROCESS FOR ITS PREPARATION AND ITS USES

BACKGROUND OF THE INVENTION

1. Field of the Invention

The present invention relates to a cosmetic or dermatological powder, to a process for its manufacture and to its uses, in particular to care for, cleanse, remove make-up from, make up and/or treat the skin, mucous membranes and/or the scalp.

2. Description of the Background

It is known in the cosmetics or dermatological field that, to remedy the defects (greasy feel, difficulty in taking up) of the anhydrous products commonly used, powders can be used which contain a large percentage of oil, these powders thus having the advantage of being comfortable to apply. However, these powders usually contain surfactants, which are potential irritant agents, and are generally rehydrated at the time of use, resulting in handling difficulties.

Moreover, make-up powders are known which have a low oil content and a high filler content and which cannot be used as care products since, in this case, they have the drawback of not being sufficiently comfortable to use because of their low content of oily phase, and of inevitably leaving a visible film on the surface of the skin.

In the field of skincare, EP-A-664,112 describes a powder based on oil, biopolymers and polysaccharides, which is obtained from an oil-in-water (O/W) emulsion and which can be used just as it is or after rehydration into an O/W emulsion. However, such a powder has the drawback of containing biopolymers chosen from proteins of animal or plant origin, which are essential to the constitution of the powder since they constitute its support. Now, the use of proteins of animal origin in cosmetic or dermatological products is avoided. In addition, these proteins does not keep well over time, and certain proteins of plant origin, such as soybean proteins, can prove to be irritant, in particular when they are used in an amount of at least 4%, which is the case in the present document.

Moreover, the powder obtained according to EP-A-664, 112 is hygroscopic, which is a drawback when it is desired to use the powder just as it is, since it has a tendency to become damp and consequently exhibits poor conservation characteristics in humid tropical countries.

Moreover, WO-A-95/28849 describes solid compositions which can be used in the food sector, which are prepared by dehydration of aqueous dispersions of starch and of oil, and which can be readily redispersed in water to form stable dispersions without requiring the use of an emulsifier. The process used according to that document consists in subjecting the mixture of starch, oil and aqueous phase to high temperatures and pressures in order to dissolve the starch completely in the aqueous phase. This technique has the drawback of requiring the use of high temperatures during the mixing of the starch, oil and aqueous phase, and these high temperatures can be particularly deleterious when the composition contains oils of plant origin which are readily oxidizable and thus sensitive to high temperatures, or when it is desired to add temperature-sensitive active agents, which is often the case in the cosmetics field. Furthermore, the powder obtained is hygroscopic and thus sensitive to the presence of water, with the same drawbacks as indicated above. In addition, in the examples cited in that document, the starch used is native starch which, besides the drawback of giving hygroscopic compositions, also has the drawback of having poor bacteriological protection.

SUMMARY OF THE INVENTION

The inventors have found, unexpectedly,that the use of modified starch provides an anhydrous cosmetic or dermatological powder which can contain at least one fatty substance and which does not have the drawback, in particular of hygroscopicity, of known powders, and for which preparation does not require complete solubilization of the starch and thus the use of high temperatures and pressures during the mixing of the starch, oil and aqueous phase.

Thus, an object of the present invention is to provide a cosmetic or dermatological powder, which comprises from 5 to 70% by weight of at least one modified starch and from 30 to 95% by weight of an oily phase comprising at least one oil, relative to the total weight of the composition.

A more complete appreciation of the invention and many of the attendant advantages thereof will be readily obtained as the same becomes better understood by reference to the following detailed description.

DETAILED DESCRIPTION OF THE INVENTION

The term "powder" refers to a solid substance divided into very fine, homogeneous particles or grains. The powder may contain less than 2% by weight protein, such as at most 0.001, 0.005, 0.01, 0.05, 0.1, 0.2, 0.5, 1.0, 1.2 or 1.5% by weight. The powder preferably contains no protein.

According to one specific embodiment of the invention, the powder comprises from 5 to 50% of modified starch and from 50 to 95% of an oily phase. These ranges include all specific values and subranges therebetween, including 10, 15, 20, 25, 30, 40, 55, 60, 70, 75, 80, 85 and 90% by weight. The powder according to the invention comprises an oily phase fixed in the modified starch.

This powder in particular has the advantages that it can be applied to any type of skin without leaving a greasy effect, despite the large amount of oil, of being quick and easy to use, of penetrating into the skin without leaving a visible film, of retaining the moisturizing properties of the fatty substances and of not requiring the addition of a liquid such as water since it can be used just as it is. In addition, the desired amount can be taken up easily.

In addition, since this powder can be obtained without an emulsifier and since it keeps well, the addition of emulsifiers and/or of preserving agents can be avoided, and a powder which is much less irritant than the standard care products can thus be obtained. Accordingly, a preferred embodiment of the present invention excludes emulsifier.

Moreover, a cosmetic product presented in this form allows the incorporation of compounds with various physicochemical properties. This product can thus comprise detergents. This makes it possible in particular to cleanse the skin while at the same time moisturizing and nourishing it. Thus, the inventive composition may be a cosmetic or dermatological product having a variety of applications and one which is not specific to one type of skin.

Moreover, compounds known to be sensitive to water and/or to oxidation, such as vitamins (vitamin C., vitamin A or their esters) or enzymes, can be incorporated into the inventive powder. These compounds are preserved for a long time in this medium and therefore do not lose their activity over time.

The powder according to the invention has a particle size (or number-average particle size) which can range in particular from about 0.1 to about 100 µm, preferably from 0.5 to 50 µm and more preferably from 1 to 10 µm. The particle size ranges include all specific values and subranges therebetween, including 0.2, 2, 5, 8, 12, 15, 20, 25, 30, 40, 60, 70, 80, 85, 90 and 95 µm. The particle size may be measured with the machine "Microtrac×100 & SRA 150" from Leeds-Northrup.

The modified starch used in the composition of the invention can be modified by one or more of the following reactions: pregelatinization, oxidation, crosslinking, or esterification.

More specifically, these reactions can be carried out in the following way:

pregelatinization by bursting the starch granules (for example drying and cooking in a drying drum);

oxidation with strong oxidizing agents leading to the introduction of carboxyl groups into the starch molecule and to the depolymerization of the starch molecule (for example by treating an aqueous starch solution with sodium hypochlorite);

crosslinking with functional agents capable of reacting with the hydroxyl groups of the starch molecules, which will thus be linked together (for example with glyceryl and/or phosphate groups);

esterification in alkaline medium in order to graft functional groups, in particular acetyl, hydroxyethyl, hydroxypropyl, carboxymethyl, octenylsuccinic.

As modified starches which can be used according to the invention, mention may be made, for example, of starches esterified with octenylsuccinic anhydride and more particularly "Aluminium Starch octenyl succinate" such as the product sold by National Starch under the name Dry-Flo, the crosslinked corn starch sold under the name Resistamyl E2 by Amylum; the potato starch esterified with a carboxymethyl group, sold under the name Supramyl P 60 by Amylum, the corn starch esterified with a hydroxypropyl group, sold under the name Merigel EF6 by Amylum; the pregelatinized starch modified with octenylsuccinic anhydride and then with a hydrophobic unit, sold under the name Natrosorb HFB by National Starch; the crosslinked and acetylated corn starch sold by Cerestar under the name C* Flo 06205. According to a preferred embodiment of the invention, the modified starches are Dry-Flo and C* Flo 06205.

For a description of starches, including modified starches, see *Kirk-Othmer Encyclopedia of Chemical Technology*, Fourth Edition, Volume 22, pp.699–719, incorporated herein by reference.

The oily phase of the inventive composition contains at least one oil. The oil used can be chosen from mineral oils such as liquid paraffin or liquid petroleum jelly, silicone oils such as volatile silicone oils, oils of plant origin (for example sweet almond oil or apricot kernel oil), oils of animal origin and synthetic oils, and mixtures thereof.

Fatty substances can be added to the oil(s), such as fatty acids, fatty alcohols, waxes such as waxes of animal origin, for instance bees wax, carnauba wax or candellila wax, mineral waxes, for instance microcrystalline waxes, and synthetic waxes, for instance polyethylene wax or silicone wax.

The powder of the present invention may also comprise one or more additives commonly used in the cosmetics and dermatological fields. Additives which may be mentioned are, for example, cosmetic or dermatological active agents, emulsifiers or surfactants, detergents, dyestuffs, including pigments, abrasive agents, antioxidants or anti-free-radical agents, fillers and fragrances. These additives can represent from 0 to 30% of the total weight of the powder, preferably from 0.5 to 15% of the total weight of the powder.

These ranges include all specific values and subranges therebetween, including 0.1, 0.2, 1, 2, 5, 10, 12, 20, and 25% by weight.

Active agents which may be mentioned are, for example, antiacne agents, antimicrobial agents, antiperspirants, astringent agents, deodorants, hair-removing agents, external analgesics, hair conditioners, skin conditioners, antisun agents, vitamins, essential fatty acids, keratolytic agents, enzymes, moisturizers, anti-inflammatories, detergents or foaming agents, fragrances, inorganic or organic matt-effect fillers and depigmenting agents.

Advantageously, the powder of the invention contains a medium which is physiologically acceptable to the skin, the scalp and/or mucous membranes.

Another subject of the invention relates to a process for manufacturing a powder, in particular a cosmetic or dermatological powder, comprising at least one modified starch and an oily phase, the process comprising (1) the preparation of an oil-in-water dispersion by mixing an oily phase comprising at least one oil in an aqueous phase comprising at least one modified starch, the oily phase/starch weight ratio ranging from 3:7 to 19:1, and (2) dehydration of the dispersion in order to obtain the powder.

The term "dispersion" refers to any oil-in-water dispersion or emulsion, i.e. any mixture of an oily phase in an aqueous phase in the presence or absence of an emulsifier.

The aqueous phase of the oil-in-water dispersion preferably represents at least 30% by weight of the dispersion.

The oily phase/starch weight ratio ranges from 3:7 to 19:1 and is preferably greater than or equal to 1. This ratio is more preferably from 1 to 19 and more preferably from 2 to 10.

According to one specific embodiment of the process, the dispersion used is such that it has a solids content of between 5 and 70 % by weight and preferably of between 10 and 60% by weight. Such a solids content makes it possible for the dispersion to have a viscosity such that it is fluid enough to be useable in the rest of the steps. These ranges for the solids content include all specific values and subranges therebetween, including 15, 20, 25, 30, 40, 50, 55 and 65% by weight.

The aqueous phase can be prepared at any temperature, i.e., 0 to 100° C. The process is preferably performed at a temperature ranging from 80° C. to 100° C.

In parallel, the oily phase may be prepared and is added to the aqueous phase which is preferably cooled to a temperature below 80° C., preferably in an amount such that the resulting dispersion has a solids content of between 5 and 70% by weight.

The dispersion is then formed by slowly mixing the aqueous and oily phases, for example by carefully incorporating the oily phase into the aqueous phase while stirring constantly.

An oil-in-water dispersion is thus obtained with a pH which depends on its composition, but is generally between 4 and 9.

The process preferably comprises a homogenization step between the preparation of the dispersion by mixing the oily phase and the aqueous phase and before dehydration of the dispersion obtained. The homogenization is advantageously carried out at high pressure, so as to reduce the average size of the droplets of the oily phase to about 350 nm or even less.

The homogenization is carried out at a pressure generally of between 300 and 600 bar, preferably of about 600 bar ($60\times10^6$ Pa), in order to obtain droplets of oily phase with an average size (on a number basis) preferably of less than 350 nm, generally ranging from 80 to 300 nm.

The dispersion thus homogenized is then dehydrated by any known process, and in particular by spraying or by freeze-drying. According to a preferred embodiment of the invention, the dehydration is carried out by spraying. In this case, the temperature of the hot air used for the drying preferably ranges from about 100° C. to about 220° C., and the outlet temperature of the powder preferably ranges from about 30° C. to about 140° C. The spraying time is very short: it is preferably less than or equal to 2 minutes.

A subject of the present invention is also a powder, in particular a cosmetic and/or dermatological powder, which can be obtained according to the process described above.

The powder obtained can be compacted in order to save volume and to make it easier to package, conserve, store and use. Before the optional compacting of the powder, it can undergo an additional granulation step with the aim of homogenizing the particle size of the powder.

The powder obtained is very stable and can be conserved for several months without any phase separation, change in color, uptake of water or other deteriorations, for example microbiological deterioration, being observed.

In addition, the water-sensitive or oxidation-sensitive active agents, such as vitamins, for instance ascorbic acid (vitamin C), green tea or enzymes, remain very stable in this type of powder.

The powder of the invention can be used directly just as it is or can be incorporated into a cosmetic and/or dermatological composition having another pharmaceutical form, such as a lotion or a W/O or O/W emulsion.

A subject of the present invention is thus also a cosmetic and/or dermatological composition comprising a powder as defined above.

The subsequent use of the powder of the invention depends on the desired aim and on the active agents which may be present. It can be used in particular to care for, cleanse, remove make-up from, make up and/or treat the human skin, scalp and/or mucous membranes.

Thus, another subject of the present invention is a cosmetic process to care for, cleanse, remove make-up from, make up and/or treat the skin, mucous membranes and/or the scalp, comprising the application of a powder as defined above to the skin, mucous membranes and/or the scalp.

Another subject of the invention is the use of the powder as defined above for the preparation of a composition intended to care for, cleanse, remove make-up from, make up and/or treat the skin, the scalp and/or mucous membranes.

Having generally described this invention, a further understanding can be obtained by reference to certain specific examples which are provided herein for purposes of illustration only and are not intended to be limiting unless otherwise specified.

EXAMPLES

Example 1

Skincare Powder

| | |
|---|---|
| Modified starch (Dry FLo) | 25% |
| Apricot oil | 75% |

In order to obtain this powder, a mixture is prepared containing 8% of modified starch and 68% of water, and the mixture is heated to 95° C., after which it is cooled to 70° C. and 24% of apricot oil is incorporated, while stirring constantly so as to obtain an oil-in-water dispersion. The dispersion is cooled to room temperature while stirring and is homogenized at a pressure of about 600 bar ($60\times10^6$ Pa), after which it is passed through a spraying machine in which the hot air is at 200° C. and the outlet temperature is 120° C.

The powder is used just as it is, not reconstituted, and constitutes a product which is effective in nourishing the skin.

Example 2

Skincare Powder

| | |
|---|---|
| Modified starch (C* Flo 06205) | 35% |
| Silicone oil (phenyltrimethicone sold under the name DC 556 Fluid by Dow Corning) | 60% |
| Ascorbic acid | 5% |

The manufacturing process is identical to that of Example 1.

A powder which can be applied to the skin in order to improve the radiance of the complexion and to smooth out fine lines is obtained. The vitamin C remains stable in this formulation: after 2 months at 45° C., less than 5% degradation is observed.

Obviously additional modifications and variations of the present invention are possible in light of the above teachings. It is therefore to be understood that within the scope of the appended claims, the invention may be practiced otherwise than as specifically described herein.

This application is based on French Patent Application Serial No. 98-01219, filed on Feb. 3, 1998, and incorporated herein by reference in its entirety.

We claim:

1. A cosmetic or dermatological powder, comprising:
   9.1 to 70% by weight, relative to the total weight of the composition, of at least one modified starch, and
   30 to 90.9% by weight, relative to the total weight of the composition, of an oily phase comprising at least one oil.

2. The powder of claim 1, which contains no protein.

3. The powder of claim 1, comprising:
   9.1 to 50% by weight, relative to the total weight of the composition, of the modified starch, and 50 to 90.9% by weight, relative to the total weight of the composition, of the oily phase.

4. The powder of claim 1, wherein the modified starch is the reaction product obtained by pregelatinizing, oxidizing, crosslinking and/or esterifying a starch.

5. The powder of claim 1, wherein the modified starch is a starch esterified with octenylsuccinic anhydride.

6. The powder of claim 1, wherein the oily phase comprises at least one oil selected from the group consisting of mineral oils, silicone oils, oils of plant origin, oils of animal origin and synthetic oils.

7. The powder of claim 1, wherein the oily phase further comprises at least one fatty substance selected from the group consisting of fatty acids, fatty alcohols and waxes.

8. The powder of claim 1, further comprising at least one additive selected from the group consisting of cosmetic or dermatological active agents, emulsifiers, detergents, dyestuffs, abrasive agents, antioxidants or anti-free-radical agents, fragrances and fillers.

9. The powder of claim 8, wherein the cosmetic or dermatological active agent is selected from the group consisting of antiacne agents, antimicrobial agents, antiperspirants, astringent agents, deodorants, hair-removing agents, external analgesics, hair conditioners, skin conditioners, antisun agents, vitamins, essential fatty acids, keratolytic agents, enzymes, moisturizers, anti-inflammatories, detergents, fragrances, inorganic or organic (matt-effect) fillers, and depigmenting agents.

10. The powder of claim 8, wherein the active agent is selected from the group consisting of ascorbic acid, retinol and its esters, enzymes and green tea.

11. A cosmetic and/or dermatological composition comprising the powder of claim 1.

12. A process for manufacturing a cosmetic and/or dermatological powder, comprising at least one modified starch and an oily phase, comprising:

(1) preparing an oil-in-water dispersion by mixing an oily phase comprising at least one oil in an aqueous phase comprising at least one modified starch, wherein the oily phase/starch weight ratio is 3:7 to 10:1, and (2) dehydrating the dispersion to obtain the powder.

13. The process of claim 12, wherein the oily phase/starch weight ratio is from 1:1 to 10:1.

14. The process of claim 12, wherein the aqueous phase of the oil-in-water dispersion represents at least 30% of the total weight of the dispersion.

15. The process of claim 12, further comprising a homogenization step between the preparation of the dispersion and before dehydration of the said dispersion.

16. The process of claim 15, wherein the homogenization is carried out at a pressure of about 600 bar.

17. The process of claim 12, wherein the dehydration is carried out by spraying.

18. The process of claim 17, wherein the dehydration is carried out in a spraying machine in which the temperature of the hot air used for the drying ranges from about 100° C. to about 220° C., and the outlet temperature of the powder ranges from about 30° C. to about 140° C.

19. A cosmetic and/or dermatological powder, obtained by the process of claim 12.

20. A cosmetic process for caring for, cleansing, removing make-up from, making-up and/or treating the skin, mucous membranes and/or the scalp, comprising applying the powder of claim 1 to the skin, mucous membranes and/or the scalp.

21. A method of treating skin, mucous membranes or the scalp, comprising applying the powder of claim 1 to the skin, mucous membranes or the scalp.

22. The powder of claim 1, wherein the amount of the oily phase is 30 to 75% by weight, relative to the total weight of the composition.

23. The powder of claim 1, wherein the amount of the oily phase is 30 to 60% by weight, relative to the total weight of the composition.

24. The process of claim 12, wherein the oily phase/starch weight ratio is 3:7 to 3:1.

25. The process of claim 12, wherein the oily phase/starch weight ratio is 3:7 to 12:7.

* * * * *